United States Patent
Kessler et al.

(10) Patent No.: US 6,880,387 B2
(45) Date of Patent: Apr. 19, 2005

(54) ACOUSTIC MICRO IMAGING METHOD PROVIDING IMPROVED INFORMATION DERIVATION AND VISUALIZATION

(75) Inventors: Lawrence W. Kessler, Buffalo Grove, IL (US); Thomas E. Adams, Lawrenceville, NJ (US); Michael G. Oravecz, Naperville, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 508 days.

(21) Appl. No.: 09/935,264

(22) Filed: Aug. 22, 2001

(65) Prior Publication Data

US 2004/0149021 A1 Aug. 5, 2004

(51) Int. Cl.$^7$ ............................................. G01N 29/06
(52) U.S. Cl. ........................... 73/105; 73/601; 382/108; 382/154; 382/147
(58) Field of Search ........................ 73/104, 105, 601; 382/108, 147, 154

(56) References Cited

U.S. PATENT DOCUMENTS

| | | | |
|---|---|---|---|
| 3,686,932 A | 8/1972 | Ries et al. | |
| 4,575,799 A * | 3/1986 | Miwa et al. | 600/442 |
| 5,115,673 A | 5/1992 | Kline et al. | |
| 5,307,680 A | 5/1994 | Drescher-Krasicka | |
| 5,454,045 A * | 9/1995 | Perkins et al. | 382/181 |
| 5,871,013 A | 2/1999 | Wainer et al. | |
| 5,999,836 A | 12/1999 | Nelson et al. | 600/407 |
| 6,032,534 A | 3/2000 | Sherwin | 73/628 |
| 6,078,681 A | 6/2000 | Silver | |
| 6,390,978 B1 * | 5/2002 | Irion et al. | 600/437 |
| 6,429,431 B1 | 8/2002 | Wilk | |
| 2001/0035871 A1 * | 11/2001 | Bieger et al. | 345/630 |
| 2002/0018588 A1 * | 2/2002 | Kusch | 382/131 |

FOREIGN PATENT DOCUMENTS

| | | | |
|---|---|---|---|
| EP | 1110508 | * | 6/2001 |
| GB | 2196206 | * | 4/1988 |
| JP | 1-139044 | * | 5/1989 |
| JP | 4-183446 | * | 6/1992 |

OTHER PUBLICATIONS

PCT Notification of Transmittal of the International Search Report or the Declaration.
TAMI from website of Sonix (http://www.sonix.com/sam/Products/Software/TAMI.htm) (undated) 2 pages.
Article Reflections, vol. III, No. 4, from web site of Sonoscan, Inc. (undatedbut admitted to be prior art to this application.) 3 pages.
Application Note No. 216 of Sonoscan Inc Copyright 1999. 3 pages. See http://www.sonoscan.com/applications/AppNotesCompositel.htm.
PCT Written Opinion.

* cited by examiner

*Primary Examiner*—Daniel S. Larkin
(74) *Attorney, Agent, or Firm*—Welsh & Katz, Ltd.

(57) ABSTRACT

A method for enhancing information derived from acoustically inspected samples comprises deriving an acoustic image of a sample, and generating a visual superposition of one or more additional images. The additional images are selected from the group consisting of an optical image, a second acoustic image in a different sized field of view form said acoustic image, an infrared image, an X-ray image, and an electron beam image.

21 Claims, 5 Drawing Sheets

ACOUSTIC MICRO IMAGING METHOD PROVIDING IMPROVED INFORMATION DERIVATION AND VISUALIZATION

BACKGROUND, OBJECTS, AND SUMMARY OF THE INVENTION

This invention has a broad range of applications, however, for convenience of explanation it will be described in the context of what is known as acoustic micro imaging ("AMI") in which an acoustic microscope is employed to detect minute features within or on the surface of an examined sample. AMI is commonly employed in material and process analysis, failure analysis, non-destructive testing, and production quality control and inspection, for example.

AMI is based upon the fact that acoustic waves traveling through a sample of homogenous material will be altered when the waves encounter an anomaly of some type. If the anomaly has a different acoustic impedance than the sample material, the waves will be reflected, refracted, deflected or scattered. If the anomaly has a different acoustic absorption characteristic than the sample material, a differential absorption of the acoustic wave will occur. Under certain conditions the wave may be converted from one form to another, as compressional wave to shear wave or surface wave. AMI takes advantage of these alterations of an interrogating acoustic wave by an anomaly to produce visual displays of the interior of an examined sample.

It is common in AMI inspection and visualization applications for the internal region of interest in an inspected sample to be small in comparison with the dimensions of the sample. In such applications it is often difficult for the user to physically correlate in space the micro location of the inspected region of interest with the macro space occupied by the sample.

An example of this is in the AMI inspection of printed circuit ("PC") boards ("PCBs"). A PCB may, for example, be twelve or more inches long and mount dozens of components. Typically only a few of the components are inspected—e.g., integrated circuits ("ICs").

The user would typically have access to visualizations of a variety of AMI "slices" taken at various depths in selected inspected components on the PCB. These visualizations often show impedance features of interest within the examined samples, such as die or die lead disbonds, cracks, epoxy underfill voids, and so forth. This is extremely valuable information, but it is uncorrelated with the PCB. The user is plagued by questions such as: Which examined components exhibit which of the visual anomalies? What is the correct spatial orientation of the acoustic visualization relative to the PCB? How does the scale of the visualized sample relate to the scale of the IC or other parts on the PCB?

A need thus exists for a method which correlates AMI micro imagery with the macro space of the inspected sample or collection of samples, with correct spatial orientation and scaling. It is an object of the present invention to meet this need.

In the design and manufacture of PCB assemblies, it is of interest to know whether the general layout of components on the board is optimum. Designers would like to know, e.g., whether the locations of the components producing the most heat are such that those components will affect the performance or reliability of other components. Under current practice, AMI inspections are performed on various PCB parts scattered across the board, but no information is available that might suggest a relationship between detected defects or anomalies on various parts. There is no simple way of predicting whether the placement of a microprocessor or power amplifier or other heat-producing element, for example, is deleteriously affecting the life or performance of adjacent components.

It is another object of the present invention to meet the described need by providing a method which makes possible the correlation of macro visualizations (such as a full PCB) with micro AMI visualizations, and which in so doing facilitates an improved understanding of interactive effects between spatially separated parts.

In current AMI practice a number of images, representing slices in X-Y planes perpendicular the Z direction of the acoustic probe, will be created at Z-various depths in an examined sample (which can include a surface slice). These X-Y slices may be closely adjacent in the Z dimension, but frequently are sufficiently spaced as to visualize different anomalies. It is not uncommon to visualize in transparent mode a chosen group of adjacent ones of these slices. Upon occasion it would be of great interest to better understand how the anomalies visualized in selected internal slices of arbitrary location correlate with surface features, or how slices (internal or surface) in different sized fields of view correlate.

It is another object of the present invention to satisfy the described need for spatial correlation between selected internal slices and surface features of the examined part, or between selected internal slices in different sized fields of view.

In certain implementations of the present invention, images formed by disparate methodologies are overlaid in a common rendering. It is still another object to rectify all correlated images to assure accurate orthography and scaling of overlaid images.

In production quality and process control, laboratory analysis, failure analysis, and other applications, as much information as possible is desired to be obtained about the parts or samples of interest. It is of obvious interest to correlate the information collected in order that additional information can be gleaned from the correlations.

It is yet another object of the present invention to provide a method for correlating information generated using disparate energy forms, including optical, infrared, acoustical, and other, and different capture techniques, including AMI and other acoustic imaging, photography, thermography, electron beam microscopy, X-ray and other.

It is a further object to provide display and visualization methods to enhance the information developed from overlays of images developed from like and/or disparate energy forms and techniques.

DESCRIPTION OF THE PREFERRED MODES OF EXECUTION OF THE INVENTION

The methods and equipment that has evolved in the field of acoustic micro imaging ("AMI") has proven to be of great value in non-destructive testing, laboratory research and testing, failure analysis, production quality control and inspection, and many other applications. The ultimate output in most applications is a visual display which is studied to extract the maximum possible information about the interior structure of an examined production part or other sample.

While a great deal of information can be gleaned from AMI visualizations of acoustic impedance and absorption features within an examined sample, in many applications the capabilities of the AMI equipment and techniques are not fully realized because the spatial context of the visualizations presented are not fully understood. Further, additional useful information can be obtained by interrogating or illuminating the specimen with other forms of energy and correlating that information with acoustically derived information.

It is a stated object to provide a method which correlates acoustic micro imagery with the macro space of the inspected sample or collection of samples. It is another stated object of the present invention to provide a method which makes possible the correlation of macro visualizations of samples, such as a full printed circuit board with micro AMI visualizations, and which in so doing facilitates an improved understanding of interactive effects between spatially separated parts. It is yet another stated object of the present invention to provide a method for correlating information generated using disparate energy forms and different capture techniques.

Figure 1:
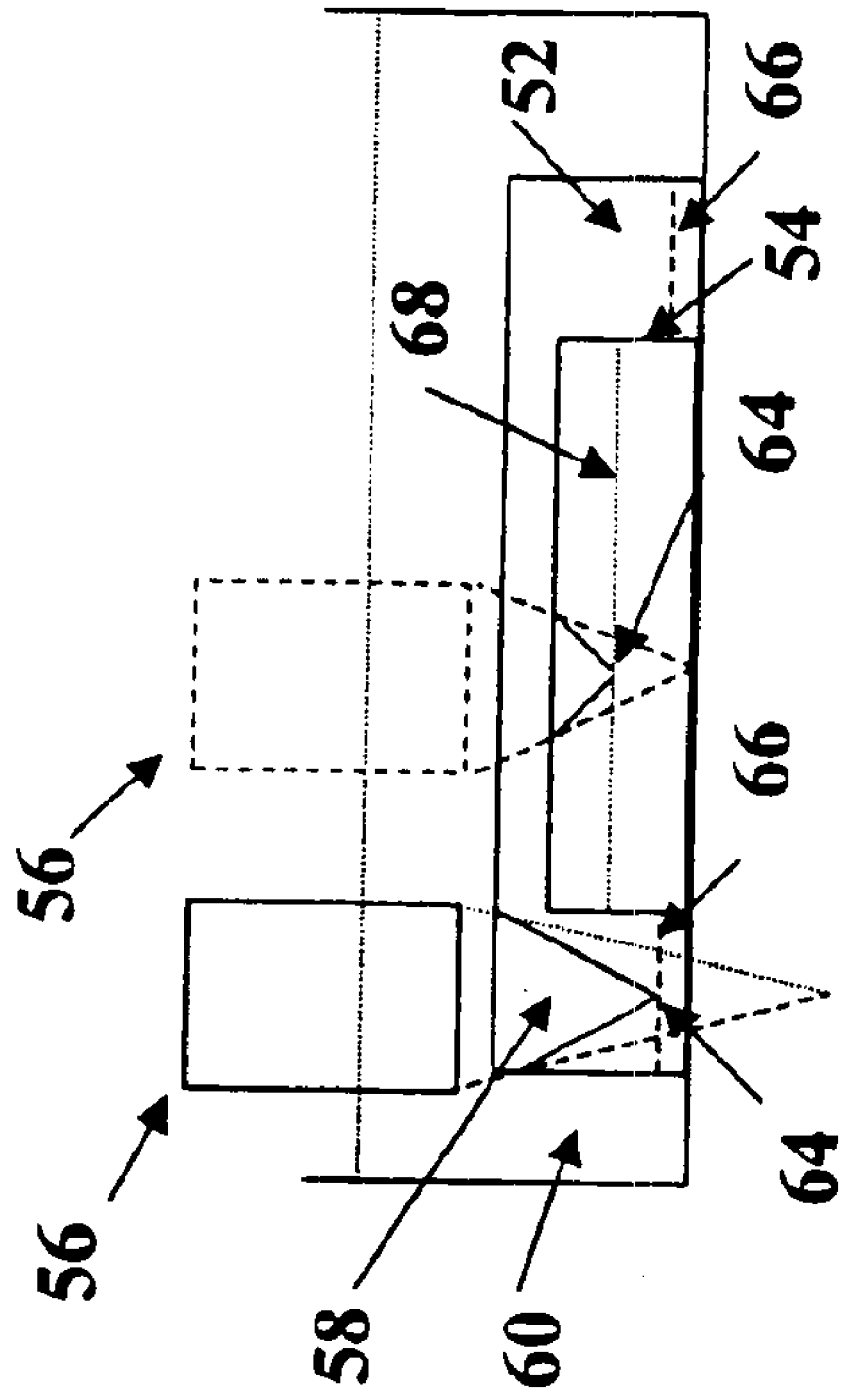
FIGS. 1 and 2 are schematic diagrams of a C-SAM instrument which may be employed in the practice of the present invention.

The methods of the present invention each center on the acquisition of an acoustic image, and in a preferred execution of the invention, an acoustic image of the type generated with the use of a scanned ultrasonic probe. FIG. 1 depicts an AMI system of a type in use today which may be employed to acquire an acoustic image of a sample to be inspected.

FIG. 1 illustrates in highly schematic form a C-Mode scanning acoustic microscope, or "C-SAM", 20 which may be employed to implement the principles of the invention. It is shown as being adapted to inspect an integrated circuit ("IC") package 22 submerged in a coupling medium 24. A pulser 26, under the control of controller 28 excites a transducer 30 to generate a pulsed ultrasonic probe 32, typically at frequencies ranging from 10 MHz or lower to 230 MHz or higher. The transducer 30 is scanned in X, Y, and Z coordinates by an X-Y-Z stage 34 through an X-Y-Z stage driver 36 under the control of controller 28.

Acoustic reflections from impedance features in the IC package 22 are sensed by a receiver 38. Acoustic reflectance signals developed by receiver 38 are in analog form. These signals will be described in detail below. The analog acoustic reflectance signals developed by receiver 38 are supplied to a multi-channel, multifunction processor 40 which gates and detects the signal. The processor 40 also adjusts the retrieved acoustic reflectance signal to correct or reduce signal amplitude errors such as may be caused by acoustic energy absorption by the examined sample. The processor 40 includes a digitizer section in which the analog signals are quantized into digital bytes for storage in a multi-channel memory 44.

To create a display, the stored data stored within memory 44 is employed to modulate a display device 48, which may be CRT monitor, for example. Alternatively, as is well known, time-of-flight data may also be displayed.

Figure 2:
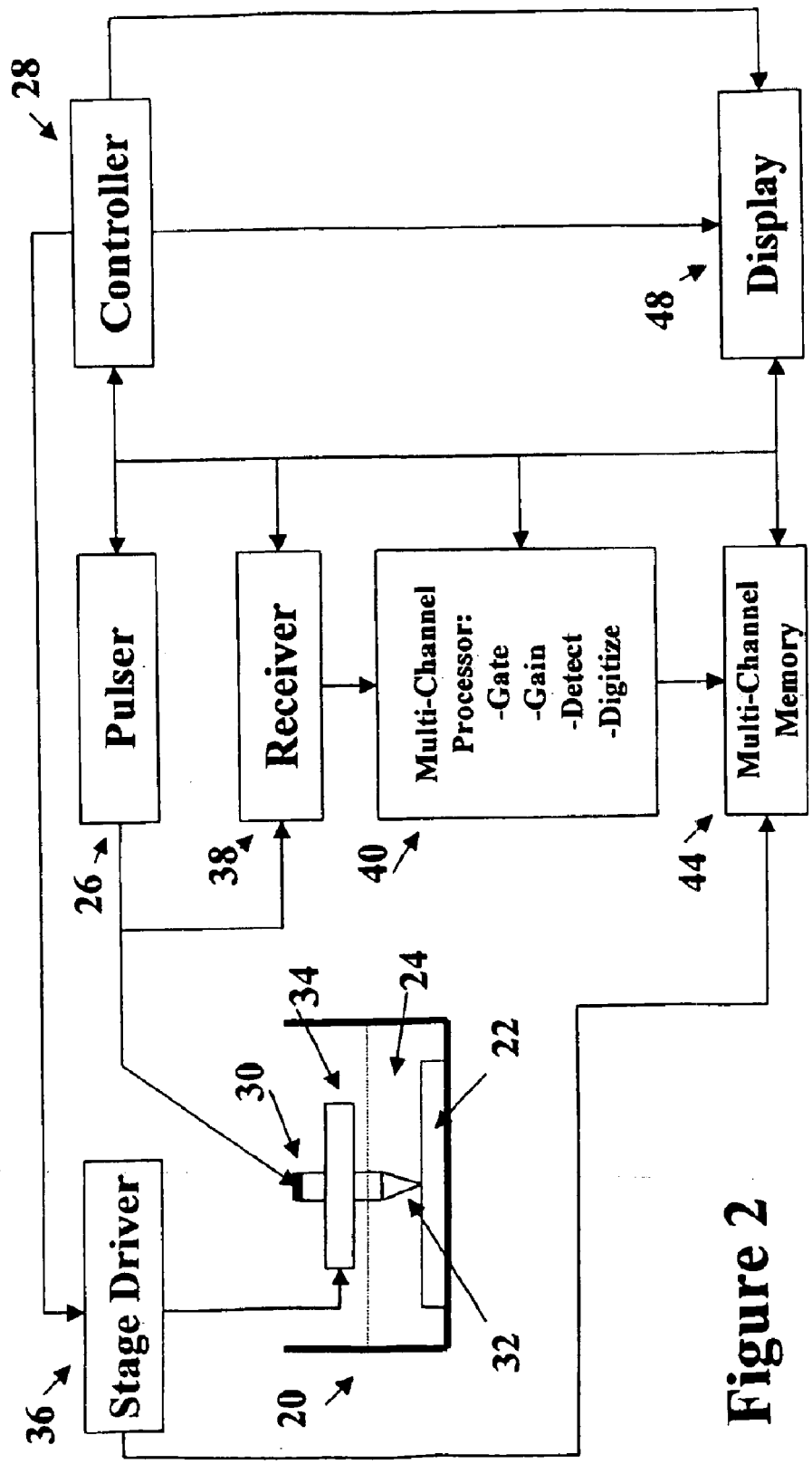

It is of note that in AMI discussions it is customary to speak or write of "scan planes" or "slices", when in fact a scan may not develop a true plane of interrogated points. FIG. 2 illustrates in highly schematic fashion the manner in which, in practice, a scanned plane can, for example, have an offset. An IC package is shown simplified as comprising a silicon die 54 encapsulated by an IC epoxy encapsulant 52. A transducer 56 emits an ultrasonic probe 58 transmitted to the IC package through a couplant such as a body 60 of water. As the acoustic index of epoxy is greater than that of water, the probe focus 64 is displaced toward the transducer 56 and scans a plane 66 within the epoxy encapsulant 52. As the transducer 56 is translated into the region of the die 54, however, the probe focus 64 is displaced closer to the transducer 56 and scans a plane 68 offset from plane 66. Because such deviations from a true plane are typically minor, for convenience it is common parlance to simply refer to a scan plane. That convention has been followed in this application.

Figure 3:
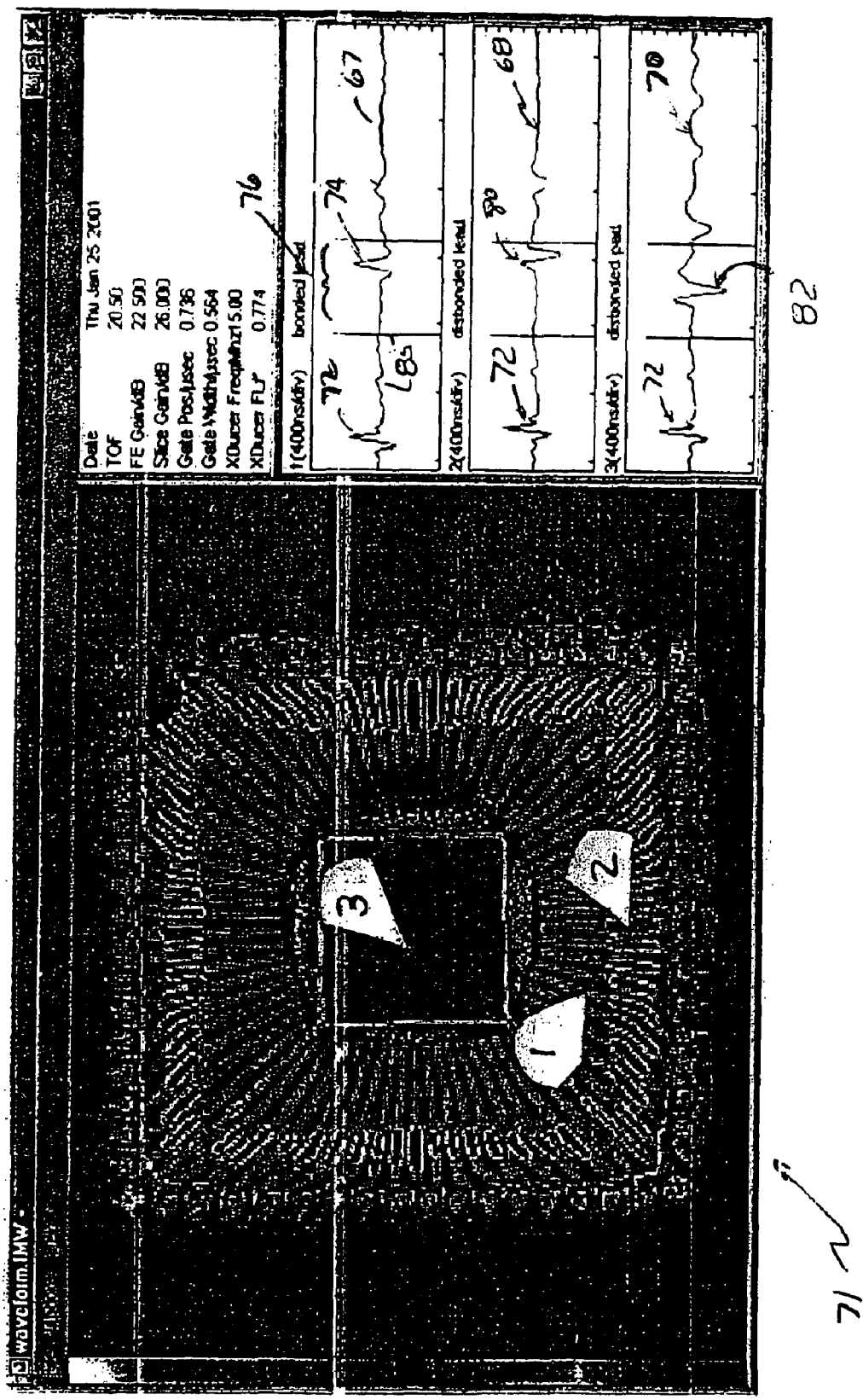
FIG. 3 is a screen print of a monitor image produced with a C-SAM instrument such as depicted in FIG. 1, illustrating the nature of the acoustic images which are produced by such an instrument.

FIG. 3 is a screen print of a monitor image 71 formed using a commercial C-SAM instrument such as shown schematically in FIG. 1. The sample inspected was an encapsulated integrated circuit having a die attached to a pad, with leads extending radially from all sides of the die.

As noted, the roundtrip "time of flight" of the acoustic pulses from transducer to sample front surface was 20.50 microseconds. The front-end ("FE") gain was set at 22.500 dB, and the slice gain at 26.000 dB. The gate was positioned at 0.736 microseconds from the front surface echo and had a width of 0.564 microseconds in order to capture a depth in the package embracing the die leads and the die-pad interface. The transducer frequency was 15 MHz and the transducer focal length was 0.774 inch.

Acoustic reflectance signals 67, 68, 70 were stimulated by the transducer at three locations, numbered "1", "2", and "3", respectively. Location "1" was on a bonded lead. The white color in the image reproduction signifies a sound bond between the inspected lead and the encapsulating material. Corresponding acoustic reflectance signal 67 shows a reflection 72 from the front surface of the package. About one microsecond later, we see a positive polarity reflection 74 from the soundly bonded lead. As the reflection 74 is within the reproduction gate 76, the reflection 74 is rendered in the image 71.

However, with the probe at position "2" over a different lead, we see in acoustic reflectance signal 68 a negative polarity reflection 80, indicating that the acoustic wave encountered an interface with a lower acoustic impedance than that of the sample material. The logical interpretation of this data is that the lead at position "2" is disbonded, and that the resulting air gap is responsible for the phase reversal of the reflection 80. Again, because the reflection 80 is within the gate, it is visualized in the image 71.

With the probe at position "3" on the die-surface interface, acoustic reflectance signal 70 shows a negative polarity reflection 82 from the interface, indicating a die-surface disbond (air gap) at the epoxy-die interface. The location of the reflection 82 closer to the front surface reflection 72 than reflection 80 is from front surface reflection 72 indicates that the die-surface interface is slightly higher (closer to the probe) than the leads at positions "1" and "2".

Thus, from the above description it is well known in the field of acoustic micro imaging to capture an X-Y set of data points, each point representing the detected peak of a gated region of an amplitude-modulated acoustic signal reflected from impedance features within the body of an insonified solid part. The set of data points may be visualized, for example on the screen of a computer monitor.

By moving the position of the gate along the time axis of the acoustic reflectance signal, a particular plane or layer within the examined part may be inspected. To increase the resolution capability of the X-Y dataset at varying depths through the solid, it is known to coincide the focus of the acoustic transducer employed with the gated region of the part.

The present invention in general terms, as executed in a preferred embodiment, is directed to a method for enhancing information derived from acoustically inspected samples. The method comprises using an ultrasonic probe to derive an acoustic image of a sample interior area or volume. One or more additional images of the sample are derived, the images being preferably optical, acoustic, infrared (thermographic), X-ray, or electron beam. A visual superposition of the one or more additional images of the sample with the acoustic image is generated. The superposed additional images are rendered in a transparent mode wherein one image can be seen through the other, or in an opaque mode wherein an image overlying another image is partially cut away to expose the underlying image.

In one preferred arrangement, the one or more additional images is an optical image of the sample exterior rendered in a mode such that impedance anomalies exhibited in the acoustic image are visible concurrently with the optical image of the sample exterior.

As noted in the BACKROUND OF THE INVENTION, one use of the invention is to enhance the information in an acoustic inspection and visualization of a PC board, in which case the one or more additional images is an optical image, preferably a digital photograph, of the sample (the PC board), and wherein the transparent mode is employed to visualize the acoustic and optical images simultaneously.

Figure 4:
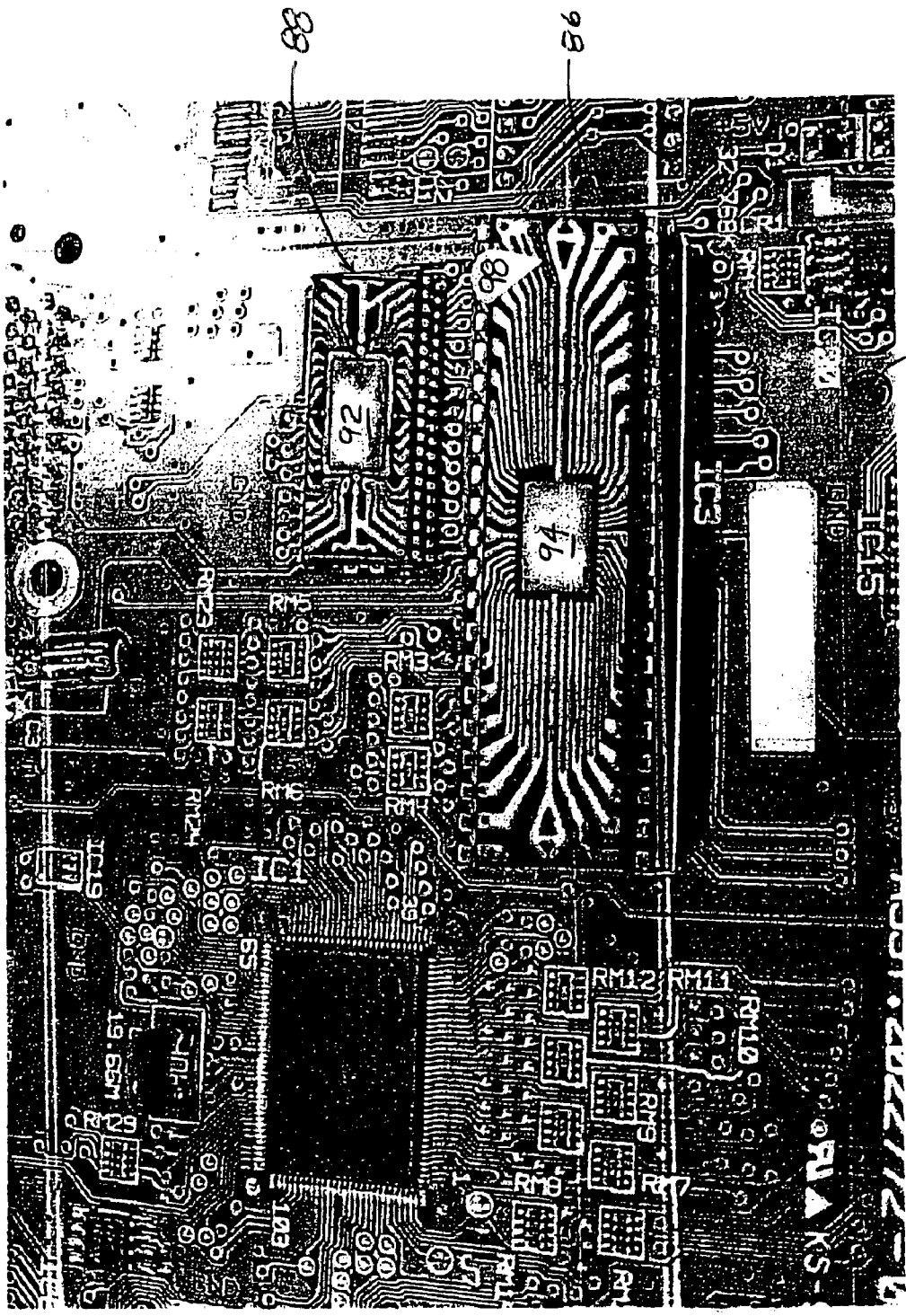
FIG. 4 is a composite acousto-optic rendering of a PC board, produced according to the teachings of the present invention.

FIG. 4 is an actual composite acousto-optic rendering of a conventional PC board 84, produced according to the method of the present invention. The PC board 84 mounts a typical number and arrangement of components and etched conductive traces. Of particular interest in FIG. 4 are two integrated circuits 86, 88 exhibiting on their respective top surfaces superposed acoustic micro images produced by a C-SAM instrument scanning the ICs in situ at the depth of the die bond and leads. On IC 86, the die bond is shown at 94 and the connecting lead bonds are shown radiating out from the die bond 94.

In the acoustic image superposed on the optical image of integrated circuit ("IC") 88, the die bond is shown at 92; the lead bonds are shown radiating out from the die bond 92.

Whereas the patent drawings do not clearly illustrate a gross disbond in a lead location numbered 98, the actual rendering clearly shows in a distinct color the disbond region. To an observer, the composite rendering of a photographic (optical) image and superposed acoustic images of impedance features at critical internal regions within the ICs 86,88 has a number of significant benefits.

First, the observer has before him or her an optical image of a PC board 84 with which the observer may be quite familiar. The observer may be aware that the PC board was acoustically inspected, but may not know which components were inspected. The observer may not have ready access to the acoustic images.

Second, even if the acoustic images were available the observer likely would not know which images were associated with which components, or if the complete component was or was not inspected, or what regions of the component were inspected. In accordance with this application of the present invention, the observer can see at a glance which components were acoustically inspected, have an accurate depiction of the results of the inspection accurately positioned in space relative the examined ICs, and will know where the defects are located on the inspected parts.

Third, if the PC board is operative and can be visualized in the described way before and after life test, it may be possible to discern that life test failures due to die disbonds are spatially correlated with a source of heat on the PC board, for example. So, through this invention, being able to effectively see inside and outside these key parts concurrently greatly enhances production quality control and inspection, research and development, and even product and process design.

Information derived through the present invention may lead to significantly improved business performance through improved product quality, reliability and performance, improved production processes, reduced warranty costs, and improved product design.

A composite acousto-optic image as described may be developed in a number of ways. The most straightforward approach is to generate a digital photographic rendering of the sample —a populated PC board, for example—from a viewpoint directly above the board. This orthographic photograph can be acquired in one frame, or if the sample is as large as a PC board, in order to minimize field edge image distortions, a seamless mosaic photograph can be created using well-known step-and-repeat and photogrammetric techniques. If it is desired to have a composite acousto-optic rendering as shown in FIG. 4 wherein the viewpoint is off-axis, the optical rendering may be acquired using well-known tilt-angle photographic techniques. A digital camera may be mounted on a 3D digitizer frame which tracks the X, Y, and Z spatial coordinates of the camera in space, and its phi and theta pointing orientations. Optimized optical systems, such as a telecentric lens system, can be used in the camera. Such systems are widely used in optical metrology because they reduce measurement or positional errors in the image.

The acoustic image is normally acquired from a viewpoint directly above the board and typically has negligible distortion. The acoustic image is processed such that its effective viewpoint is coincident with the perspective from which the optical rendering was acquired.

The optical and acoustic images are correlated by creating artificial or natural reference points which are acoustically scanned and visually marked. Alternatively, well-known pattern recognition techniques may be employed to align the optical and acoustic images. In sum, for optimum results the optical and acoustic images must be manipulated to have like acquisition viewpoints (apparent or actual), scale and orientation.

To elevate information development to another level, composite 3D acousto-optic virtual images of a sample can be created which can be rotated in space and viewed from all sides.

Techniques are well known and commercially employed in AMI to create a 3D "acoustic solid" of a sample. This process begins by "slicing" the part into as many horizontal sections as desired. Typically ten slices are adequate for thin samples such as integrated circuits, however, up to two hundred slices or more can be made on commercially available AMI equipment. Equipment software can be set to divide the part into equal thickness slices. Each slice is then automatically scanned with the focus and gate optimized for each specific slice depth. As in C-Mode scanning, the reflectance signals are gated and peak amplitude values are stored.

With commercially available 3D computer modeling software and hardware, the slices are reconstructed into an acoustic solid. The acoustic solid can be rotated to any desired angle of view. With this software, an operator can also visualize cross-sections of the acoustic solid. Sectioning can take many different forms—a single horizontal, vertical, or diagonal section can be removed. Multiple sections or "bits" can be removed which are correlated to material properties, rather than by geometry. For example, an operator might remove the entire molding compound from an IC package and still leave intact the image of a crack within the molding compound.

To create a composite acousto-optic solid which can be viewed from any desired angle, a correlative optical 3D dataset must be generated from which a 3D rendering can be created which has the same viewpoint (apparent or actual), scale, and orientation as the acoustic solid. Suitable three-dimensional photographic cameras and software are in widespread use today. The essence of what must be accomplished is simply to capture a 3D dataset which represents optical images of the sample from various viewpoints in a sphere of possible viewpoints surrounding the sample. The location in space and orientation of the camera are accurately recorded for each image acquired.

These desiderata can be achieved, for example, by mounting a video camera head on a 3D digitizing system. A suitable video camera head and associated video control, recording and display equipment is the DXC-LS1/1 manufactured by Sony Electronics Inc. of Park Ridge, N.J., USA. A suitable 3D digitizer is the Microscribe 3D Desktop Digitizing System manufactured by Immersion Corporation of San Jose, Calif., USA.

If animated rotational viewing is desired, well-known computer interpolation techniques are employed to create a seamless rendition.

The 3D acoustic and optical datasets are then integrated to create the desired superposition of optical and acoustic images. As in the "still" acousto-optic composite image described above, the optical and acoustic images may be accurately correlated by creating artificial or natural reference points which are acoustically scanned and visually marked, or pattern recognition techniques may be employed to align the optical and acoustic images.

With this 3D arrangement by which an acousto-optic virtual solid is created, the observer can view acoustic anomalies from any angle and see them in relation to the exterior of the sample and its surroundings.

Figure 5:
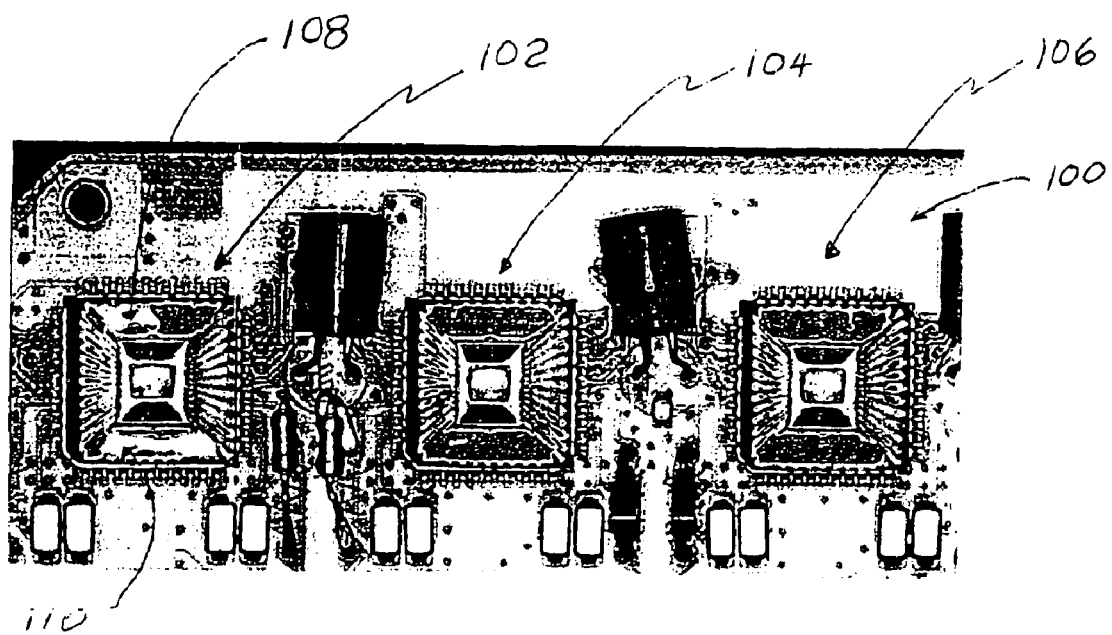
FIG. 5 is a composite image produced according to the present invention in which two acoustic images are superposed, one of the surface of a PC board and the other of impedance features within certain board components.

The present invention also contemplates superposing with an acoustic image one or more additional acoustic images. FIG. 5 is another composite visualization made according to the teachings of the present invention. FIG. 5 represents pictorially the superposition of two acoustic images actually generated with a C-SAM instrument—one, an acoustic image of the entire top surface of a PC board 100, and the other, an acoustic image taken at a depth associated with the die and lead-frames within three identical ICs 102, 104, 106. A gross internal defect in IC 102 can readily be observed at locations 108 and 110.

The surface scan may be made with a large depth of field transducer and a signal gate wide enough to encompass all surface features. If the user desires to have all internal impedance features in focus, a large depth of field transducer and wide gate would also be selected for the internal scan.

If a narrow slice at a given depth in the examined part is to be displayed with the surface acoustic image, the user would employ a narrower depth of field transducer, a narrower gate set for the prescribed depth and a setting of the transducer probe focus at the prescribed depth. These operating parameters will yield the sharpest image of the prescribed internal scan plane.

However, for the internal acoustic image, it may be desired to have in sharp focus impedance features in various internal regions of the sample located at different Z-depths. In that case, the system would be programmed or manually operated to adjust focus, gain and gate location and width for different levels in selected regions within the sample. Through this process, the internal acoustic image will show all features of interest in various regions of the sample in focus in the composite image.

As the same C-SAM instrument was employed to create both images in successive scans, the two acoustic images are in perfect registry. The depth separation in the direction of the ultrasonic probe is sufficient that completely different acoustic impedance feature information is provided. By having the images in superposition and presented in the transparent mode—that is, wherein the overlying image is transparent to the underlying image so that both can be seen simultaneously—the full information from both scans is available to the observer.

As noted above, rather than employing the transparent mode of presentation, an "opaque mode" could have been employed wherein the overlying image is opaque to the underlying image. In that case, regions of the overlying image would be cut away or peeled back to reveal the underlying image. The optimum presentation mode employed depends upon the application.

In a modification of the FIG. 5 execution, rather than employing one internal acoustic image and a surface acoustic image, two or more internal acoustic images captured in different sized fields of view could be overlaid. There the benefit of being able to spatially correlate and visualize different internal impedance anomalies in different sized fields of view is considered to be greater than the benefit of having improved correlation with the top surface of the PC board.

In accordance with yet another execution of the method of the invention, an acoustic image is combined with an infrared image. Again, reverting to the example of a PC board as the examined and visualized sample, an acoustic image is made of an IC such as a high performance microprocessor which is known to generate significant power when operating. The PC board is then activated, as in a life test. While in life test, a digital infrared image may be acquired using, e.g., a commercial thermography camera.

The images acquired by the thermographic camera will clearly reveal the location and intensity of the regions where heat is created in the IC during operation. Then, an acoustic image may be created at a chosen depth in the IC. A second (or further) acoustic image can be created at a different depth or with different operating parameters. Using the techniques described, the infrared image is combined with either or both of the acoustic images, or the acoustic images are combined with each other. In this way, the user can abstract as much information as possible about the effects of the heat generated during the operation of the IC on defect creation or modification. It is known from AMI studies that defects which are benign before operation of an IC, can become lethal during operation of the IC due to the effects of heat on captured moisture, for example.

The infrared images can be acquired in essentially the same way as described above with respect to optical image capture. This is not surprising, as infrared radiation may be viewed simply as non-visible light adjacent the long wavelength end of the visible spectrum.

In lieu of an optical image to capture image of the surface of a sample, in applications where microscopic surface features are of interest, an electron beam microscope ("EBM") image may be combined with an acoustic image. In this application, the focus is on comparing microscopic external features with microscopic internal features to deduce, for example, whether there is any correlation between microscopic external surface features and internal acoustic impedance or absorption anomalies or defects.

Since both EBM and C-SAM are similar in basic principles of operation, differing primarily in the different energy forms employed, correlation of the digital datasets and generation of superposed electron beam and acoustic images is straightforward.

There are applications where it is desired to correlate energy loss characteristics with acoustic reflection characteristics. It is yet another object of the present invention to provide a method for superposing an acoustic image of the reflection type with a transmission acoustic image, an X-ray image, or other image which characterizes energy loss differences in a sample.

Transmission imaging is one of the standard modes for many AMI instruments available today. This mode employs a detector beneath the sample, rather than (or in addition to) a detector positioned to capture acoustic reflections from impedance features within the sample. By locating the acoustic detector below the sample, the only acoustic energy detected is that which has not been absorbed, reflected, scattered, or otherwise prevented from passing through the sample. Acoustic transmission images are particularly useful in applications where gross disbonds or other defects are of interest.

In accordance with another aspect of the present invention, an acoustic reflection image is acquired by a C-SAM instrument, for example, is combined with a transmission acoustic image. Commercial equipment is available from the assignee of the present invention which captures both reflection and transmission images during the same inspection process. The reflection and transmission images are conventionally displayed separately. There has been no known recognition until this invention of the value of combining these images into a composite overlay which simultaneously shows anomalies in both transmission and reflection. Although more difficult than the superposition of reflection and transmission acoustic images, in accordance with the present invention, an X-ray absorption image may also be created and superposed on an acoustic image.

To enhance the information derived from composite images generated according to the teachings of the present invention, it is an object of the invention to process the signals for the constituent images to form a display signal, and then to process the display to create special visual effects in the display.

A variety of known image enhancement techniques may be employed to glean further information from displayed composite images created following this invention. These include edge enhancement, filtering, interpolation, line doubling, cross-correlation, and shadowing.

While particular embodiments of the present invention have been shown and described, it will be obvious to those skilled in the art that other changes and modifications may be made without departing from the invention in its broader aspects. The appended claims are intended to cover all such changes and modifications that fall within the scope of the invention.

What is claimed is:

1. A method for enhancing information derived from acoustically inspected samples, comprising: deriving acoustic image of a sample; and generating a visual superposition of one or more additional images of the sample selected from the group consisting of: an optical image, a second acoustic image in a different sized field of view from said acoustic image, or in a different mode of acquisition, an infrared image, an X-ray image, and an electron beam image, wherein said superposed images are rendered in an opaque mode, and wherein an image overlying another image is partially cut away to expose the underlying image.

2. The method defined by claim 1 wherein an ultrasonic probe is used, and said derived acoustic image is of a sample interior area or volume.

3. The method defined by claim 1 wherein one or more of said additional one or more additional images is a derived image.

4. The method defined by claim 3 wherein an ultrasonic probe is used, and said derived acoustic image is of sample inferior or volume.

5. A method for enhancing information derived from acoustically inspected samples, comprising: using an ultrasonic probe, deriving acoustic image of a sample interior area or volume; and generating a visual superposition of one or more additional images of the sample selected from the group consisting of: an optical image, a second acoustic image in a different sized field of view from said acoustic image, or in a different mode of acquisition, an infrared image, an X-ray image, and an electron beam image, wherein the sample is a PC board, and one of said one or more additional images is a digital photograph of the sample exterior rendered in mode such that impedence anomalies exhibited in said acoustic image are visible concurrently with said digital photograph of the sample exterior.

6. The method defined by claim 5 wherein one or more of said one or more additional images is a derived image.

7. The method of claim 6 wherein a transparent mode is employed to visualize the digital photographic image and the acoustic image simultaneously.

8. The method defined by claim 5 wherein a transparent mode is employed to visualize the digital photographic image and the acoustic image simultaneously.

9. A method for enhancing information derived from acoustically inspected samples, comprising: using an ultrasonic probe, deriving acoustic image of a sample interior area or volume; and generating a visual superposition of one or more additional images of the sample selected from the group consisting of: an optical image, a second acoustic image in a different sized field of view from said acoustic image, or in a different mode of acquisition, an infrared image, an X-ray image, and an electron beam image, wherein one of said additional images is an infrared image of the sample rendered in a mode such that impedance anomalies exhibited in said acoustic image are visible concurrently with the infrared image of the sample.

10. The method defined by claim 9 further including an additional image that is an optical image of the exterior of the sample such that impedance anomalies exhibited in said acoustic image of the sample interior area or volume are visible concurrently with the optical and infrared images.

11. The method defined by claim 10 wherein the sample is a printed circuit board.

12. The method defined by claim 10 wherein one or more of said one or more additional images is a derived image.

13. The method defined by claim 12 wherein the sample is a printed circuit board.

14. The method defined by claim 9 wherein one or more of said one or more additional images is a derived image.

15. A method for enhancing information derived from acoustically inspected samples, comprising: using an ultrasonic probe, deriving acoustic image of a sample interior area or volume; and generating a visual superposition of one or more additional images of the sample selected from the group consisting of: an optical image, a second acoustic image in a different sized field of view from said acoustic image, or in a different mode of acquisition, an infrared image, an X-ray image, and an electron beam image, wherein one of said additional images is an electron optical image of the sample exterior rendered in a mode such that impedance anomalies exhibited in said acoustic image are visible concurrently with the electron optical image of the sample exterior.

16. The method defined by claim 15 wherein one or more of said one or more additional images is a derived image.

17. A method for enhancing information derived from acoustically inspected samples, comprising: using an ultrasonic probe, deriving acoustic image of a sample interior area or volume; and generating a visual superposition of one or more additional images of the sample selected from the group consisting of: an optical image, a second acoustic image in a different sized field of view from said acoustic image, or in a different mode of acquisition, an infrared image, an X-ray image, and an electron beam image, wherein one of said additional images is a second acoustic image generated at the same or different depth as said acoustic image, but with a larger or smaller field of view, and wherein the second acoustic image is an image of the sample exterior rendered in a mode such that impedance anomalies exhibited in said acoustic image of the sample interior area or volume are visible concurrently with the acoustic image of the sample exterior.

18. The method defined by claim 17 wherein one or more of said one or more additional images is a derived image.

19. A method for enhancing information on acoustically inspected simples, comprising: using an ultrasonic probe deriving first electrical signal characterizing an acoustic image of a sample interior area or volume; deriving one or more additional electrical signals characterizing one or more images of the sample selected from the group consisting of: optical, acoustic, infrared, X-ray, and electron beam; procesing said first signal and said one or more additional signals to develop a display signal; using the display signal to generate a visual display; and processing said display signal to create special visual effects in said display; wherein one of said additional images is an optical image of the sample exterior, wherein the sample is a printed circuit board, and wherein the optical image is a digital photograph.

20. A method for enhancing information on acoustically inspected simples, comprising: using an ultrasonic probe deriving first electrical signal characterizing an acoustic image of a sample interior area or volume; deriving one or more additional electrical signals characterizing one or more images of the sample selected from the group consisting of: optical, acoustic, infrared, X-ray, and electron beam; procesing said first signal and said one or more additional signals to develop a display signal; using the display signal to generate a visual display; and processing said display signal to create special visual effects in said display, wherein one of said additional images is an electron optical image of the sample.

21. A method for enhancing information on acoustically inspected simples, comprising: using an ultrasonic probe deriving first electrical signal characterizing an acoustic image of a sample interior area or volume; deriving one or more additional electrical signals characterizing one or more images of the sample selected from the group consisting of: optical, acoustic, infrared, X-ray, and electron beam; procesing said first signal and said one or more additional signals to develop a display signal; using the display signal to generate a visual display; and processing said display signal to create special visual effects in said display, wherein a first of said additional images is an optical image of the exterior of the sample and a second of said additional images is a infrared image of the sample.

* * * * *